United States Patent [19]

Baker et al.

[11] Patent Number: 6,103,937
[45] Date of Patent: Aug. 15, 2000

[54] NICKEL CATALYZED ADDITION OF -NH- CONTAINING COMPOUNDS TO VINYL AND ARYL HALIDES

[75] Inventors: Ralph Thomas Baker, Los Alamos, N. Mex.; Sigríður Sóley Kristjánsdóttir, Wilmington, Del.

[73] Assignee: E. I. du Pont de Nemours and Company, Wilmington, Del.

[21] Appl. No.: 09/214,101

[22] PCT Filed: Jun. 30, 1997

[86] PCT No.: PCT/US97/11521

§ 371 Date: Dec. 29, 1998

§ 102(e) Date: Dec. 29, 1998

[87] PCT Pub. No.: WO98/00399

PCT Pub. Date: Jun. 8, 1998

Related U.S. Application Data

[60] Provisional application No. 60/021,170, Jul. 1, 1996.
[51] Int. Cl.$^7$ ................................................ C07C 209/00
[52] U.S. Cl. ............................ 564/408; 564/212
[58] Field of Search ..................... 564/408, 212

[56] References Cited

U.S. PATENT DOCUMENTS 3,914,311  10/1975  Coulson et al. .

FOREIGN PATENT DOCUMENTS 0 385 835  9/1990  European Pat. Off.  ...... C07C 209/10
0 613 719  9/1994  European Pat. Off.  ......... B01J 31/24

OTHER PUBLICATIONS

H.–J. Cristau et al., *Chemical Abstracts*, 128, No. 15, Abstract No. 198354t, Oct. 9, 1995.
E. A. Krasilnikova et al., *Chemical Abstracts*, 119, No. 23, Abstract No. 250037a, Dec. 6, 1993.
R. Cramer et al., *Journal of Organic Chemistry*, 40, No. 16, 2267–2273, Oct. 8, 1975.
T. Ogawa et al., *Chemistry Lett.*, 1443, 1991.
M. Kosugi et al., *Chem. Lett.*, 927, 1983.
F. Paul et al., *J. Am. Chem. Soc.*, 116(13), 5969–70, 1994.
J. Louie et al., *Tetrahedron Lett.*, 36(21), 3609–12, 1995.
J.F. Hartwig et al., *J. Am. Chem. Soc.*, 117(19), 5373–5374, 1995.
J. P. Wolfe et al., *J. Org. Chem.*, 61(3), 1133–1135, 1996.
A. S. Guram et al., *Angew. Chem. Int. Ed. Engl.*, 34(12), 1348–1350, 1995.
A. J. Arduengo et al., *J. Am. Chem. Soc.*, 113, 361–363, 1991.
A. J. Arduengo et al., *J. Am. Chem. Soc.*, 114, 5530–5534, 1992.

*Primary Examiner*—Paul J. Killos

[57] ABSTRACT

A process for producing unsaturated nitrogen containing compounds such as enamides, enamines and aryl amineslamides is disclosed. A vinyl halide or aryl halide is reacted with an —NH— containing compound in the presence of a catalytic amount of a catalyst precursor composition comprising a zero-valent nickel and an organophosphine or carbene ligand. One step coupling of vinyl halides and aryl halides with —NH— containing compounds is made possible by practice of the invention.

31 Claims, No Drawings

NICKEL CATALYZED ADDITION OF -NH- CONTAINING COMPOUNDS TO VINYL AND ARYL HALIDES

This application claims benefit of Provisional Application Ser. No. 60/021,170 filed Jul. 1, 1996.

FIELD OF INVENTION

The present invention generally relates to a process for the production of enamides, enarnines, aryl amines and aryl amides by coupling a vinyl halide or aryl halide with an —NH— or —NH$_2$— containing compound using a ickel catalyst.

BACKGROUND OF THE INVENTION

Enamines and enamides are useful synthetic intermediates of use to the agrochemical, pharmaceutical, and other fine chemical industries. Previously, enamine and enamide compounds have been prepared by: a) addition of amine or amide to an epoxide followed by dehydration; b) direct addition of —NH— containing compounds to alynes; c) Curtius reaction of α, β-unsaturated azides; or d) Beckmann rearrangement of α, β-unsaturated oximes. Each of these methods requires several synthetic steps for the synthesis of enamides or enamines and some suffer from lack of regiospecificity.

Prior to the instant invention, it was known in the art that Cu(I) compounds could be used as stoichiometric reagents to effect the coupling of aryl bromides and —NH— containing compounds. This chemistry was extended to vinyl bromides by Ogawa et al (Ogawa, T.; Kiji, T.; Hayami, K.; and Suzuki, H.; Chemistry Lett. 1991, p. 1443) who reported the coupling of vinyl bromides with the potassium salt of an acidic amide in the presence of a stoichiometric amount of copper iodide to provide enamides.

The coupling of aryl halides and an —NH— containing compound has also been accomplished catalytically using a base and a palladium (Pd) catalyst. This catalyst system, however, is not known or reported to couple vinyl halides and —NH— containing compounds. Kosugi, M.; Kameyama, M.; and Migita, T.; Chem Lett., 1983, p. 927 reported the Pd catalyzed coupling of tin amides and aryl halides to form aryl amines. Several other references have disclosed the Pd catalyzed coupling of amines and aryl halides in the presence of a strong base to form aryl amines (e.g., see Paul, Frederic; Patt, Joe; and Hartwig, John F.; J. Am. Chem. Soc., 1994, 116(13), pp. 5969–70; Louie, Janis; and Hartwig, John F.; Tetrahedron Lett., 1995, 36(21), pp. 3609–12; Hartwig, John F.; and Paul, Frederic; J. Am. Chem. Soc. 1995, 117(19), pp. 53734; Wolfe, John P.; and Buchwald, Stephen L.; J. Org. Chem., 1996, 61(3), pp. 1133–5; Guram, Anil S.; Rennels, Roger A.; and Buchwald, Stephen L.; Angew. Chem., Int. Ed. Engl., 1995, 34(12), pp. 1348–50).

A. J. Arduengo, et al., J. Am. Chem. Soc., vol. 113, p. 361–363 (1991) and A. J. Arduengo, et al., J. Am. Chem. Soc., vol. 114, p. 5530–5534 (1992) report the synthesis of (1,3-disubstitutedimidazol-2-ylidene) carbenes.

The present invention provides for the use of a nickel catalyst complex rather than the more expensive palladium catalysts of the prior art and allows for the one step coupling of vinyl halides in addition to aryl halides. Other objects andadvantges of the present invention will become apparent to those skilled in the art upon reference to the detailed description which hereinafter follows.

SUMMARY OF THE INVENTION

The present invention relates to a process for the production of unsaturated nitrogen containing compounds comprising: reacting a compound containing an —NH— or —NH$_2$— gunctional group next to a carbon sp$^2$ center with a compound of the formula

where X is either chloride, bromide or iodide;
R$_1$ is either hydrogen, an alkyl group, or an aryl group;
R$_2$ is independently selected from hydrogen, methyl or trimethylsilyl; and
R$_3$ is an optionally substituted aryl group;
in the presence of a stoichiometric amount of a base and a catalytic amount of a catalyst precursor composition comprising a zero-valent nickel and an organophosphine or carbene ligand.

The invention also relates to a process for the production of unsaturated nitrogen containing compounds comprising: reacting the salt of a compound containing an —NH— or —NH$_2$— functional group next to a carbon sp$^2$ center with a compound of the formula

where X is either chloride, bromide or iodide;
R$_1$ is either hydrogen, an alkyl group or an aryl group;
R$_2$ is independently selected from hydrogen, methyl or trimethylsilyl; and
R$_3$ is an optionally substituted aryl group;
in the presence of a catalytic amount of a catalyst precursor composition comprising a zero-valent nickel and an organophosphine or carbene ligand.

The unsaturated nitrogen containing compounds are preferably enamides, enamines, aryl amines or aryl amides.

DETAILED DESCRIPTION OF THE PREFERRED EMBODIMENTS

Abbreviations used hereafter are listed and defined below as follows:
CD$_3$CN Acetonitrile-d3
NO$_2$CD$_3$ Nitromethane-d3
COD 1,5-Cyclooctadiene
DBU 1,8-Diazabicyclo[5.4.0]undec-7-ene
DBN 1,5-Diazabicyclo[4.3.0]non-5-ene
DMF Dimethylformamide
DMSO Dimethyl sulfoxide
KO$^t$Bu Potassium tert-butoxide
Pcy$_3$ Tricyclohexylphosphine
P(napth)$_3$ Tri(1-naphthyl)phosphine
P(ptol)$_3$ Tri(o-tolyl)phosphine
THF Tetrahydrofuran
NMP N-methyl-2-pyrrolidinone
The following terms as used herein are defined as follows:
"Alkyl" means an alkyl group up to and including 12 carbons. Common examples of such alkyl groups include methyl, ethyl, propyl, isopropyl, butyl, s-butyl, isobutyl, pentyl, neopentyl, hexyl, heptyl, isoheptyl, 2-ethylhexyl, cyclohexyl and octyl.
"Aryl" means a group defmed as a monovalent radical formed conceptually by removal of a hydrogen atom from a hydrocarbon that is structurally composed entirely of one or more benzene rings. Common examples of such hydrocarbons include benzene, biphenyl, terphenyl, naphthalene, phenyl naphthalene, and naphthylbenzene.

"Heteroaryl" refers to unsaturated rings of 5 or 6 atoms containing one or two O and S atoms and/or one to four N atoms provided that the total number of hetero atoms in the ring is 4 or less, or bicyclic rings wherein the five or six membered ring containing O, S, and N atoms as defined above is fused to a benzene or pyridyl ring. Common examples are furan and thiphene.

"Hydrocarbyl" means a monovalent group containing only carbon and hydrogen, and may be chiral or achiral. Unless otherwise stated, it is preferred that hydrocarbyl (and substituted hydrocarbyl) groups contain 1 to 30 carbon atoms.

"Substituted" means a group that is substituted and contains one or more substituent groups that do not cause the compound to be unstable or unsuitable for the use or reaction intended. Substituent groups which are generally useful include nitrile, ether, ester, halo, amino (including primary, secondary and tertiary amino), hydroxy, oxo, vinylidene or substituted vinylidene, silyl or substituted silyl. nitro, nitroso, sulfinyl, sulfonyl, sulfonic acid alkali metal salt, boranyl or substituted boranyl, and thioether.

By an "inert functional group" is meant a group such as acyl [—C(O)-alkyl] which does not cause the appropriate compound to be unstable or unsuitable for its use. A typical definition of a functional group may be found in R. T. Morrison, et al., Organic Chemistry, 6th Ed., Prentice Hall, Englewood Cliffs, N.J., 1992, p. 167–168 the contents of which are incorporated herein.

The phrase "more electronegative than carbon" as measured by the familiar Pauling Electronegativity Scale, see for instance J. E. Huheey, Inorganic Chemistry, 2nd Ed., Harper and Row, New York, 1978, p. 162. Also included within the definition of "more electronegative than carbon" are groups that are effectively more electronegative than carbon even though the atom bound directly to the imidazole ring may by itself not be more electronegative than carbon. See for instance J. E. Huheey, Inorganic Chemistry, 2nd Ed., Harper and Row, New York, 1978, p. 164. An atom that is more electronegative than carbon is bound to the carbon atom at the 4 or 5 position of the imidazole ring.

In Formulas I–V and other carbenes disclosed herein, the "colon" at the two position of the ring represents the two electrons of the carbene group.

The instant invention allows for the one step coupling of either a vinyl halide or an aryl halide with an —NH— containing compound in the presence of a catalytic amount of a zero-valent nickel organophosphine or zero-valent nickel carbene complex and a stoichiometric amount of a base. Alternatively, the salt of the —NH— containing compound can also be coupled with the vinyl, heteroaryl or aryl halide in the presence of a catalytic amount of a zero-valent nickel organophosphine or zero-valent nickel carbene complex but in the absence of a base. As used herein, a "catalytic amount" is defined as no more than 75% of the stoichiometric amount.

The —NH— containing substrates of the invention are generally defined as compounds containing an —NH— or —NH$_2$ functional group next to a carbon sp$^2$ center. Examples include primary and secondary amides, anilines, imidazoles, carbamates, amidines, guanidines, amino thiazolines, and ureas. Preferred are amides, imidazoles, and carbamates. However, compounds derived from coupling an alkylamine (e.g., dimethylamine) with a vinyl halide (e.g., styryl bromide) can also be produced. For instance, for —NH— substrate 15 set forth below, dimethylamine originates from the catalyzed decomposition of the DMF solvent.

The vinyl halide substrate of the invention is of the formula $R_1R_2C=CR_2X$ where X is either chloride, bromide or iodide, $R_1$ is either hydrogen, an alkyl group, an aryl group, or an heteroaryl group, and $R_2$ is independently selected from hydrogen, methyl or trimethylsilyl. Alkyl groups can be straight chain or branched. In a preferred embodiment, X is bromide, $R_1$ is phenyl (Ph) and both of $R_2$ are hydrogen.

The aryl halides are of the formula $R_3$—X where $R_3$ is an optionally substituted aryl group and X is Cl, Br or I. Optional substitutions on the aryl group include, but are not limited to, alkyl, phenyl, alkyl or aryl ether, thioether, and halogen and halogenated alkyl groups. In a preferred embodiment, X is iodide and $R_3$ is a phenyl group which bears an electron-withdrawing substituent such as $CF_3$.

The zero-valent nickel organophosphine catalysts comprise a zero-valent nickel complexed with an organophosphine ligand, optionally prepared in-situ. The organophosphine ligand preferably comprises a trialkyl phosphine, substituted triaryl phosphine, or a tris-heteroaromatic phosphine. Alternatively, it can also be a mixed P—N or P—S ligand where N is imine, pyridine or amine, S is a thioether, and P is one of the organophosphine groups already described. The organophosphine ligand can be either monodentate or polydentate.

Preferred embodiments include large, bulky phosphine groups such as tricyclohexylphosphine, tri(1-naphthyl) phosphine, and tri(o-tolyl)phosphine. Most preferred embodiments include large, bulky electron-rich phosphine groups such as tricyclohexylphosphine.

The zero-valent nickel carbene catalysts of the invention comprise a zero-valent nickel complexed with an carbene ligand, optionally prepared in-situ.

The carbene are compounds according to Formulas I–V set forth below:

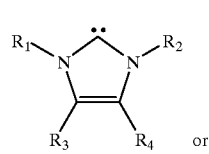

I

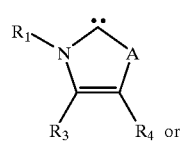

II

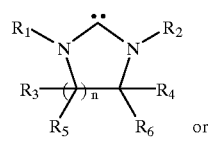

III

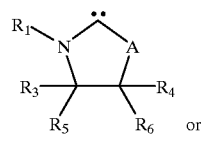

IV

-continued

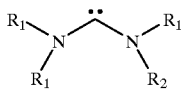

V wherein:
R¹ and R² are each independently hydrocarbyl or substituted hydrocarbyl;
R³, R⁴, R⁵ and R⁶ are independently an element more electronegative than carbon, a substituted element more electronegative than carbon, hydrogen, hydrocarbyl, substituted hydrocarbyl or an inert functional group;
n is an integer from 1 to 4; and
A is S or O.

Preferred carbene ligands are those of Formulas I, II and III. More preferred are those of Formula I Most preferred carbene ligands are those of Formula I where R¹ and R² are methyl, mesityl, or adamantane, and R³ and R⁴ are independently hydrogen or methyl.

The carbene ligands can be prepared or generated using techniques well known in the art (e.g., for imidazol-2-ylidenes see Arduengo, A. J. III, et. al., J. Am. Chem. Soc., 1994, 116, p 4391; for imidazol-2-ylidenes and larger saturated systems see Arduengo, A. J., III, et al., J. Am. Chem. Soc., 1995, 117, p 11027; for acyclic diaminocarbenes see Alder, R. W et al., Angew. Chem., 1996, 108, p 1211; for benzoxazol-2-ylidenes and oxazol-2-ylidenes see Hahn, F. E., Tamm, M. J., Organomet. Chem. 1993, 456, pg. C11; for thizaol-2-ylidenes see Arduengo, A. J., III et al., Liebigs Ann., 1997, p 365; for cyclopropen-2-ylidenes see Tamm, M et al., J. Organomet. Chem. 1995, 501, p 309; for monoaminocarbene complexes see Gabor, B et al., Angew. Chem., Int. Ed. Engl. 1991, 30, p 1666; and for a general review of metal-carbene complexes see Lappert, M. F., J. Organomet. Chem. 1988, 358, p 185; all of which are herein incorporated by reference).

The zero-valent nickel catalyst can be prepared or generated using techniques well known in the art (see, e.g., U.S. Pat. Nos. 3,496,217, 3,631,191, 3,846,461, 3,847,959, and 3,903,120 which are herein incorporated by reference). Zero-valent nickel compounds that contain ligands which can be displaced by the claimed ligand are the preferred source of zero-valent nickel. One such preferred zero-valent compound is $Ni(COD)_2$ which is well known in the art. Alternatively, divalent nickel compounds may be combined with a reducing agent and are then able to serve as suitable sources of nickel in the reaction. Suitable divalent nickel compounds include compounds of the formula $NiY_2$ where Y is halide, carboxylate, or acetylacetonate. Suitable reducing agents include metal borohydrides, metal aluminum hydrides, metal alkyls, Zn, Fe, Al, Na, and $H_2$. Elemental nickel, preferably nickel powder, when combined with a halogenated catalyst such as described in U.S. Pat. No. 3,903,120 is also a suitable source of zero-valent nickel. Divalent nickel compounds of the formula NiLRBr or $NiL_2RBr$ where L is an organophosphine or carbene ligand of the groups defined above and R is either an aryl or a vinyl group are also suitable sources of zero-valent Ni catalyst.

The reaction can be run in solution phase with a stoichiometric amount of a base of basicity equal or greater than about 20 $pK_a$ in acetonitrile. Generally, temperatures of between about 50–150° C. can be used for the reaction. Suitable non-limiting solvents include toluene, DMF, xylene, DMSO, THF, acetonitrile and nitromethane.

Presently preferred embodiments of the instant invention include in molar parts: 5 parts $Ni(COD)_2$, 10 parts $Pcy_3$, 100 parts styryl bromide, 200 parts of the —NH— containing substrate and 200 parts $KO^tBu$ in DMF at about 80–130° C.; or alternatively, 5 parts $Ni(COD)_2$, 10 parts $Pcy_3$, 100 parts styryl bromide, 200 parts of the —NH— containing substrate and 200 parts DBU in toluene at about 100–130° C.

EXAMPLES

All of the following non-limiting examples were conducted in the same manner and on the same scale as Example 1 provided below for reactions using DBU or DBN as the base, or as Example 2 for reactions using $KO^tBu$ as the base, with the exception of Examples 94–126, as described below. The same catalyst was used for all examples except as specifically noted below. The substrates listed in the tables are shown below and are identified in the tables by caption number. Isomers identified in the tables are the cis/trans (E/Z) isomers which are illustrated as "∽" in the chemical structures. Where only one product was identified, it was assumed to be the trans isomer as over time, all the isomeric mixtures identified tended to isomerize to the trans.

Product yields, as measured by gas chromatographic analysis (GC), only include the —NH— products that are neutral at the end of the reaction. When anionic products were formed, the reaction mixture was treated with hydrochloric acid and the product reanalyzed by GC. Where this was performed, the resulting numbers are denoted by an "*" in the tables. All percentages are expresssed as mol percent unless otherwise specified.

EXAMPLE 1

200 µl of a 1.0 M solution of trifluoroacetamide in DMF and 400 µl of a 0.2 M solution of β-bromostyrene in DMF were placed in a glass vial. 27 mg (0.24 mmol) $KO^tBu$ were added followed by addition of 200 µl of the catalyst solution. The catalyst solution was formed by combining 0.04 M $Ni(COD)_2$ and 0.08 M $Pcy_3$ in a 1:2 toluene/DMF solution. A color change indicating complex formation was seen when the catalyst solution was prepared, consistent with the results reported in the art. The reaction mixture was heated at 85° C. for 1.5 hrs. GC and GC/MS (mass spectroscopy) analysis showed 98% conversion to 2,2,2-trifluoro-N-(2-phenylethienyl)-acetamide.

EXAMPLE 2

16 mg (0.73 mmol) of p-iodotoluene, 16 mg (0.18 mmol) 2-oxazolidinone, and 31 mg (0.20 mmol) DBU were dissolved in 2 ml toluene. 0.5 ml of the catalyst solution was added. The catalyst solution was formed by combining 2 mg $Ni(COD)_2$ and 8.1 mg M $Pcy_3$ in 0.5 ml of toluene. A color change indicating complex formation was seen when the catalyst solution was prepared, consistent with the results reported in the art. The reaction was then heated at 100° C. for 30 hrs. GC and GC/MS analysis showed 22% conversion to 3-(4-methylphenyl)-2-oxazolidinone.

EXAMPLES 3–93
NH Substrates (—NH—containing compounds)
The following additional —NH— substrates were used in the tables provided below:
1
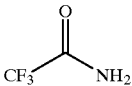
2
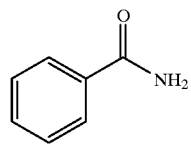
3
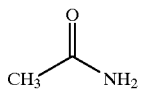
4
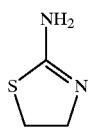
5
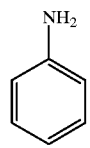
6
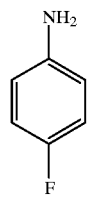
7
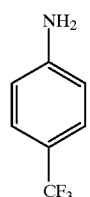
8
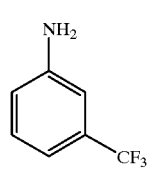
9
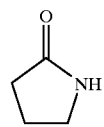
10
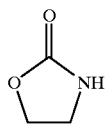
11
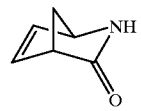
12
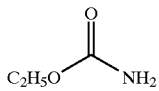
13
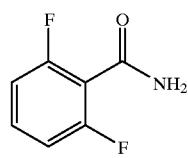
14
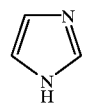
15
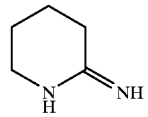
16
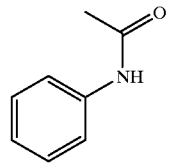
17
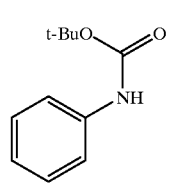
X Substrates (Vinyl Halides or Aryl Halides)
The following additional X substrates were used in the tables provided below:
i
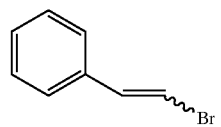
ii

iii 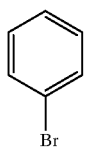
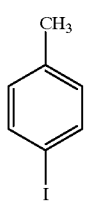
iv 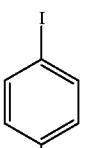
v 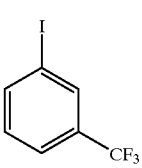
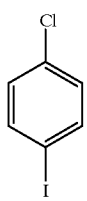
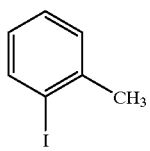
vi 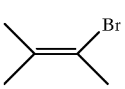
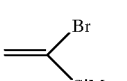
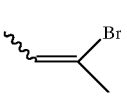
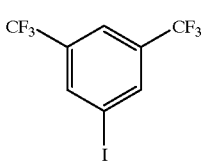
vii 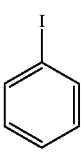
viii 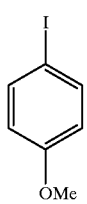
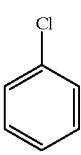
ix 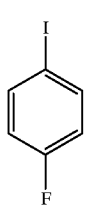
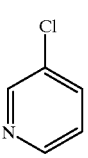
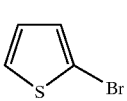

TABLE I

| Example | X | NH | Base | Solvent | Temp., °C. | Time, hrs. | Product Yield(%)-mol | Comments | Notes |
|---|---|---|---|---|---|---|---|---|---|
| 3 | i | 1 | DBU | Toluene | 105 | 15 | 17.3 | 2 isomers | |
| 4 | i | 1 | DBU | THF | 105 | 15 | 21.3 | 2 isomers | |
| 5 | i | 1 | DBU | CD$_3$CN | 105 | 15 | 31.1 | 2 isomers | |
| 6 | i | 1 | DBU | NO$_2$CD$_3$ | 105 | 15 | 43.0 | 1 product | |
| 7 | i | 1 | DBU | DMF | 120 | 16 | 11.3 | 2 isomers | a |
| 8 | i | 1 | DBU | Xylene | 120 | 16 | 18.5 | 2 isomers | b |
| 9 | i | 1 | DBU | Xylene | 120 | 16 | 9.9 | 2 isomers | c |
| 10 | i | 1 | DBN | Xylene | 120 | 16.5 | 26.0 | 2 isomers | |
| 11 | xviii | 5 | DBU | Toluene | 150 | 48 | 40 | 1 product | |
| 12 | i | 2 | DBU | Xylene | 130 | 16.5 | 12.4 | 2 isomers | |
| 13 | i | 16 | DBU | Toluene | 110 | 70 | 50 | 2 isomers | |
| 14 | i | 2 | DBU | DMF | 130 | 16.5 | 12.7 | 2 isomers | |
| 15 | i | 17 | KO$^t$Bu | DMF | 110 | 40 | 50 | 2 isomers | |
| 16 | i | 2 | DBU | DMF | 130 | 16.5 | 12.2 | 2 isomers | d |
| 17 | i | 2 | DBU | DMF | 130 | 39 | 13.8 | 2 isomers | d |
| 18 | i | 2 | DBU | Xylene | 120 | 31 | 27.8 | 2 isomers | |
| 19 | i | 2 | DBU | Xylene | 130 | 41 | 11.2 | 2 isomers | |
| 20 | i | 2 | DBU | Xylene | 140 | 41 | 6.8 | 2 isomers | |
| 21 | i | 3 | DBU | Toluene/THF | 110 | 132 | 8.0 | 2 isomers | |
| 22 | i | 4 | DBU | Xylene | 120 | 17 | 4.5 | 2 isomers | |
| 23 | i | 4 | DBU | Xylene | 120 | 90 | 4.5 | 2 isomers | |
| 24 | i | 9 | DBU | Xylene | 120 | 17 | 9.9 | 2 isomers | |
| 25 | i | 9 | DBU | Xylene | 120 | 90 | 21.2 | 2 isomers | |
| 26 | ii | 1 | DBU | Toluene-d8 | 105 | 49.5 | 2.4 | 1 product | e |
| 27 | iv | 1 | DBU | Xylene | 115 | 17 | 13.7 | 1 product | |
| 28 | iv | 1 | DBU | Xylene | 115–120 | 64 | 6.8 | 1 product | |
| 29 | v | 1 | DBU | Xylene | 115 | 17 | 0.96 | 1 product | |
| 30 | v | 1 | DBU | Xylene | 115–120 | 64 | 1.3 | 1 product | |

TABLE II

| Example | X | NH | Base | Solvent | Temp., °C. | Time, hrs. | Product yield(%)-mol | Comments | Notes |
|---|---|---|---|---|---|---|---|---|---|
| 31 | vi | 1 | DBU | Xylene | 115 | 17 | 1.3 | 1 product | |
| 32 | vi | 1 | DBU | Xylene | 115–120 | 64 | 1.0 | 1 product | |
| 33 | vi | 1 | DBU | Xylene | 115 | 17 | 10.9 | 1 product | |
| 34 | vi | 1 | DBU | Xylene | 115–120 | 64 | 12.8 | 1 product | |
| 35 | i | 1 | DBU | Toluene | 85 | 44 | 14.5 | 2 isomers | |
| 36 | i | 10 | DBU | Toluene | 100 | 60 | 43.4 | 1 product | |
| 37 | i | 11 | DBU | Toluene | 100 | 60 | 15.6 | 1 product | |
| 38 | i | 9 | DBU | Toluene | 100 | 60 | 4.5 | 1 product | |
| 39 | i | 6 | DBU | Toluene | 100 | 44 | 43.5 | 1 product | |
| 40 | i | 8 | DBU | Toluene | 100 | 44 | 10.0 | 1 product | |
| 41 | i | 2 | DBU | Toluene | 100 | 44 | 10.0 | 2 isomers | |
| 42 | i | 3 | DBU | Toluene | 100 | 44 | 12.0 | 1 product | |
| 43 | iv | 10 | DBU | Toluene | 100 | 30 | 22.0 | 1 product | |
| 44 | iv | 11 | DBU | Toluene | 100 | 30 | 3.2 | 1 product | |
| 45 | iv | 6 | DBU | Toluene | 100 | 30 | 14.5 | 1 product | |
| 46 | iv | 7 | DBU | Toluene | 100 | 30 | 5.1 | 1 product | |
| 47 | iv | 8 | DBU | Toluene | 100 | 30 | 7.4 | 1 product | |
| 48 | iv | 1 | DBU | Toluene | 100 | 44 | 18.0 | 1 product | |
| 49 | iv | 2 | DBU | Toluene | 100 | 110 | 26.0 | 1 product | |
| 50 | iii | 1 | DBU | Toluene | 85 | 20 | 4.1 | 1 product | |
| 51 | iii | 2 | DBU | Toluene | 100 | 44 | 7.7 | 1 product | |
| 52 | iii | 3 | DBU | Toluene | 100 | 44 | 9.3 | 1 product | |
| 53 | iii | 2 | DBU | Toluene | 80 | 44 | 7.0 | 2 isomers | |
| 54 | ii | 10 | DBU | Toluene | 100 | 30 | 6.2 | 1 product | |
| 55 | ii | 6 | DBU | Toluene | 100 | 30 | 14.9 | 1 product | |
| 56 | i | 10 | DBU | Toluene | 60 | 1 | 71 | 1 product | |
| 57 | xii | 10 | DBU | Toluene | 100 | 42 | 26 | | |
| 58 | xiv | 10 | DBU | Toluene | 100 | 42 | 20 | | |
| 59 | xiii | 10 | DBU | Toluene | 100 | 42 | 21 | | |
| 60 | xiv | 10 | DBU | Toluene | 100 | 42 | 20 | | |

TABLE III

| Example | X | NH | Base | Solvent | Temp., °C. | Time, hrs. | Product yield(%)-mol | Comments | Notes |
|---|---|---|---|---|---|---|---|---|---|
| 61 | vi | 1 | KO$^t$Bu/0.5,18-crown-6 | Xylene | 120 | 18 | 7.2 | 2 isomers | |
| 62 | i | 1 | KO$^t$Bu/1,18-crown-6 | Xylene | 120 | 16 | 16.2 | 2 isomers | |
| 63 | i | 1 | KO$^t$Bu/2,18-crown-6 | Xylene | 120 | 16 | 0.33 | 2 isomers | |
| 64 | i | 1 | KO$^t$Bu/3,18-crown-6 | Xylene | 120 | 16 | 7.5 | 2 isomers | |
| 65 | i | 2 | KO$^t$Bu | DMF | 110 | 5 | 40.0 | 2 isomers | |
| 66 | i | 2 | KO$^t$Bu/2,18-crown-6 | Toluene | 110 | 5 | 23.0 | 2 isomers | |
| 67 | i | 2 | KO$^t$Bu | DMF | 110 | 17 | 6.10 (90.8)* | 2 isomers | |
| 68 | i | 2 | KO$^t$Bu/2,18-crown-6 | Toluene | 110 | 17 | 43.8 (86.8)* | 2 isomers | |
| 69 | i | 1 | KO$^t$Bu | THF/1% H$_2$O | 105 | 15 | 18.1 | 2 isomers | |
| 70 | i | 1 | KO$^t$Bu | DMF | 110 | 5 | 65.8 | 2 isomers | |
| 71 | i | 1 | KO$^t$Bu | DMF | 110 | 17 | 54.7 (91.4)* | 2 isomers | |
| 72 | i | 1 | KO$^t$Bu | DMSO | 80 | 0.5 | 54* | | |
| 73 | i | 1 | KO$^t$Bu | DMSO | 80 | 2.5 | 57.6* | | |
| 74 | i | 1 | KO$^t$Bu | DMSO | 80 | 4 | 53* | | |
| 75 | i | 1 | KO$^t$Bu | NMP | 80 | 0.5 | 8.4* | | |
| 76 | i | 1 | KO$^t$Bu | NMP | 80 | 1.5 | 15.2* | | |
| 77 | i | 1 | KO$^t$Bu | NMP | 80 | 2.5 | 39.8* | | |
| 78 | i | 1 | KO$^t$Bu | NMP | 80 | 4 | 39.8* | | |
| 79 | i | 1 | KO$^t$Bu | DMF | 85 | 0.5 | 69* | | |
| 80 | i | 1 | KO$^t$Bu | DMF | 85 | 1.5 | 82* | | |
| 81 | i | 1 | KO$^t$Bu | DMF | 85 | 2.5 | 98* | | |
| 82 | i | 1 | KO$^t$Bu | DMF | 85 | 3.5 | 98* | | |
| 83 | i | 2 | KO$^t$Bu | DMF | 85 | 0.5 | 95* | | |
| 84 | i | 2 | KO$^t$Bu | DMF | 85 | 1.5 | 90* | | |
| 85 | i | 2 | KO$^t$Bu | DMF | 85 | 2.5 | 95* | | |
| 86 | i | 2 | KO$^t$Bu | DMF | 85 | 3.5 | 95* | | |
| 87 | i | 12 | KO$^t$Bu | DMF | 110 | 20.5 | 18.0 | | |
| 88 | i | 12 | KO$^t$Bu | DMF | 110 | 86.5 | 16.5* | | |
| 89 | i | 13 | KO$^t$Bu | DMF | 110 | 20.5 | 50.0 | | |
| 90 | i | 13 | KO$^t$Bu | DMF | 110 | 86.5 | 44* | | |
| 91 | i | 14 | KO$^t$Bu | DMF | 110 | 21 | 20.8 | | |
| 92 | i | 15 | KO$^t$Bu | DMF | 100 | 16 | 54 | | f |
| 93 | i | 15 | KO$^t$Bu | DMF | 100 | 40 | 49* | | f |

TABLE NOTES a. The catalyst used in the reaction was 1 equivalent P(o-tol)$_3$ to 1 equivalent Ni(COD)$_2$.

b. The catalyst used in the reaction was 2 equivalents P(o-tol)$_3$ to 1 equivalent Ni(COD)$_2$.

c. The catalyst used in the reaction was 3 equivalents P(o-tol)$_3$ to 1 equivalent Ni(COD)$_2$.

d. 1 equivalent [CH$_3$(CH2)$_3$]$_4$NBr to 1 equivalent Ni(COD)$_2$ was added to the starting system.

e. The ratio of the R$_3$—X to —NH— was 3:1. The product was N,N' disubstituted.

f. The product is styryldimethylamine derived from coupling of dimethylamine with styrylbromide. Dimethylamine originates from the catalyzed decomposition of the DMF solvent.

EXAMPLES 94–126

Examples 94–126 were run similar to Example 2 except for the following changes. Unless noted differently, a 10% (mole percent) catalyst loading of nickel carbene complex was used. The catalyst was generated in situ by mixing Ni(COD)$_2$ and carbene in a 1:1 ratio. The reaction mixture was heated at 85° C. overnight and the products analyzed by GC. Carbene ligands used are as follows:

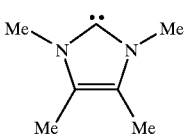

I

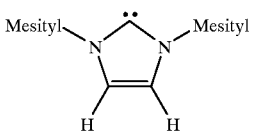

II

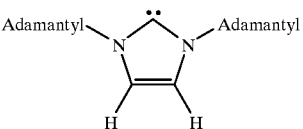

III

TABLE IV

| Example | X | NH | Ligand | Product yield(%)-mol | Notes |
|---|---|---|---|---|---|
| 94 | i | 10 | I | >98 | |
| 95 | " | " | II | >98 | |
| 96 | " | " | III | >98 | |
| 97 | i | 5 | I | >98 | a |
| 98 | " | " | II | >98 | a |
| 99 | " | " | III | >98 | a |
| 100 | i | 1 | I | >98 | b |
| 101 | " | " | II | 93 | b |
| 102 | " | " | III | 95 | b |
| 103 | i | 10 | I | 12 | |

TABLE IV-continued

| Example | X | NH | Ligand | Product yield(%)-mol | Notes |
|---|---|---|---|---|---|
| 104 | " | " | II | 36 | |
| 105 | " | " | III | 14 | |
| 106 | iii | 5 | I | 68 | |
| 107 | " | " | II | 92 | |
| 108 | " | " | III | 29 | |
| 109 | iii | 1 | I | 32 | |
| 110 | " | " | II | 20 | |
| 111 | " | " | III | 12 | |
| 112 | xv | 10 | I | 27 | |
| 113 | " | " | II | >98 | |
| 114 | " | " | III | 24 | |
| 115 | xv | 5 | I | 40 | |
| 116 | " | " | II | 36 | |
| 117 | " | " | III | 7 | |
| 118 | xv | 1 | I | 29 | |
| 119 | " | " | II | 37 | |
| 120 | " | " | III | 20 | |
| 121 | xvi | 1 | II | 0 | |
| 122 | xvii | 1 | II | 0 | |
| 123 | xvi | 10 | II | 10% | |
| 124 | xvii | 10 | II | 5% | |
| 125 | xvi | 5 | II | 40% | |
| 126 | xvii | 5 | II | 40% | |

TABLE NOTES a. GC integration unclear b. Product peak in GC overlapped by DBU peak—verified by running with DBN as the base The inventive examples indicate that zero-valent nickel complexes are catalytic in nature rather than stoichiometric and that one step coupling of vinyl halides and aryl halides can occur.

COMPARATIVE EXAMPLES (A–E)

Comparative examples of the prior art (A–C) were conducted in the same manner as the previous inventive examples except for the use of 5 % $CuBr(CH_3)S$ complex with 10% $Pcy_3$ instead of $Ni(COD)_2$ complex. The low yields indicate that Cu(I) systems, as taught in the art, are stoichiometric rather than catalytic. Additional comparative examples of the prior art (D–E) were conducted in the same manner as the previous inventive examples except for the use of Pd(0) complex with $Pcy_3$ instead of $Ni(COD)_2$ complex. The absence of product indicates that Pd phosphine complexes, as taught in the art, do not allow for one step coupling of vinyl halides and amides.

TABLE IV

| Comp. Example | X | NH | Base | Solvent | Temp., °C. | Time, hrs. | Product yield(%)-mol | Comments | Notes |
|---|---|---|---|---|---|---|---|---|---|
| A | i | 1 | DBU | Xylene | 120 | 14 | 0.46 | 2 isomers | |
| B | iii | 1 | DBU | Xylene | 120 | 14 | 2.30 | 1 product | |
| C | iii | 1 | DBU | Xylene | 120 | 36.5 | 3.40 | 1 product | |
| D | i | 1 | $KO^tBu$ | DMF | 85 | 19 | 0 | | |
| E | i | 1 | $KO^tBu$ | DMF | 85 | 86 | 0 | | |

Although particular embodiments of the present invention have been described in the foregoing description, it will be understood by those skilled in the art that the invention is capable of numerous modifications, substitutions and rearrangements without departing from the spirit or essential attributes of the invention. Reference should be made to the appended claims, rather than to the foregoing specification, as indicating the scope of the invention.

We claim:

1. A process for the production of unsaturated nitrogen containing compounds comprising:
    reacting a compound containing an —NH— or —NH$_2$— functional group next to a carbon sp$^2$ center with a compound of the formula $R_1R_2C=CR_2X$ or $R_3$—X where X is either chloride, bromide or iodide;
    $R_1$ is either hydrogen, an alkyl group or an aryl group;
    $R_2$ is independently selected from hydrogen, methyl or trimethylsilyl; and
    $R_3$ is an optionally substituted aryl group;
    in the presence of a stoichiometric amount of a base and a catalytic amount of a catalyst composition comprising a zero-valent nickel and an organophosphine ligand.

2. The process of claim 1 wherein the unsaturated nitrogen containing compound is selected from the group consisting of enamides, enamines, aryl amines and aryl amides.

3. The process of claim 1 wherein the compound containing —NH— or —NH$_2$— functional groups is selected from the group consisting of primary and secondary amides, anilines, imidazoles, carbamates, amidines, guanidines, amino thiazolines and ureas.

4. The process of claim 1 wherein the base is selected from the group consisting of 1,8-diazabicyclo[5.4.0]undec-7-ene, 1,5-diazabicyclo[4.3.0]non-5-ene, and potassium tert-butoxide.

5. The process of claim 1 wherein the catalyst composition is a complex of Ni(1,5-cyclooctadiene)$_2$ and tricyclohexylphosphine.

6. The process of claim 1 wherein X is bromide, $R_1$ is a phenyl group and both of $R_2$ are hydrogen.

7. The process of claim 1 wherein X is iodide and $R_3$ is a phenyl group substituted with $CF_3$.

8. A process for the production of unsaturated nitrogen containing compounds comprising:

reacting the salt of a compound containing an —NH— or —$NH_2$— functional group next to a carbon $sp^2$ center with a compound of the formula

$R_1R_2C=CR_2X$ or $R_3$—X where X is either chloride, bromide or iodide;

$R_1$ is either hydrogen, an alkyl group or an aryl group;

$R_2$ is independently selected from hydrogen, methyl or trimethylsilyl; and $R_3$ is an optionally substituted aryl group;

in the presence of a catalytic amount of a catalyst composition comprising a zero-valent nickel and an organophosphine ligand.

9. The process of claim 8 wherein the unsaturated nitrogen containing compound is selected from the group consisting of enamides, enamines, aryl amines and aryl amides.

10. The process of claim 8 wherein the catalyst precursor composition is a complex of $Ni(1,5\text{-cyclooctadiene})_2$ and tricyclohexylphosphine.

11. The process of claim 8 wherein X is bromide, $R_1$ is a phenyl group and both of $R_2$ are hydrogen.

12. The process of claim 8 wherein X is iodide and $R_3$ is a phenyl group substituted with $CF_3$.

13. A process for the production of unsaturated nitrogen containing compounds comprising:

reacting mono or dialkylamine with a compound of the formula

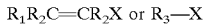

$R_1R_2C=CR_2X$ or $R_3$—X where X is either chloride, bromide or iodide;

$R_1$ is either hydrogen, an alyl group or an aryl group;

$R_2$ is independently selected from hydrogen, methyl or trimethylsilyl; and $R_3$ is an optionally substituted aryl group;

in the presence of a stoichiometric amount of a base and a catalytic amount of a catalyst composition comprising a zero-valent nickel and an organophosphine ligand.

14. The process of claim 13 wherein the unsaturated nitrogen containing compound is selected from the group consisting of enamides, enainines, aryl amines and aryl amides.

15. The process of claim 13 wherein the base is selected from the group consisting of 1,8-diazabicyclo[5.4.0]undec-7-ene, 1,5-diazabicyclo[4.3.0]non-5-ene, and potassium tert-butoxide.

16. The process of claim 13 wherein the catalyst precursor composition is a complex of $Ni(1,5\text{-cyclooctadiene})_2$ and tricyclohexylphosphine.

17. The process of claim 13 wherein X is bromide, $R_1$ is a phenyl group, and both of $R_2$ are hydrogen.

18. The process of claim 13 wherein X is iodide and $R_3$ is a phenyl group substituted with $CF_3$.

19. A process for the production of unsaturated nitrogen containing compounds comprising:

reacting a compound containing an —NH— or —$NH_2$— functional group next to a carbon $sp^2$ center with a compound of the formula

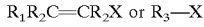

$R_1R_2C=CR_2X$ or $R_3$—X where X is either chloride, bromide, or iodide;

$R_1$ is either hydrogen, an alkyl group or an aryl group;

$R_2$ is independently selected from hydrogen, methyl or trimethylsilyl; and $R_3$ is an optionally substituted aryl group;

in the presence of a stoichiometric amount of a base and a catalyst composition comprising comprising a zero-valent nickel and a carbene ligand selected from the group consisting of

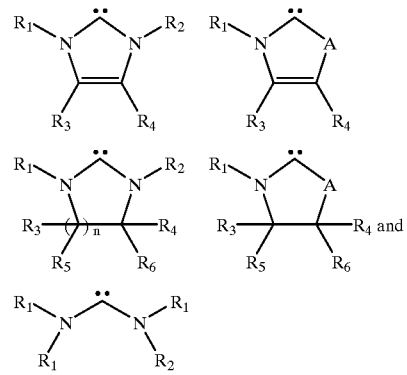

wherein:

$R^1$ and $R^2$ are each independently hydrocarbyl or substituted hydrocarbyl;

$R^3$, $R^4$, $R^5$ and $R^6$ are independently an element more electronegative than carbon, a substituted element more electronegative than carbon, hydrogen, hydrocarbyl, substituted hydrocarbyl or an inert functional group;

n is an integer from 1 to 4; and

A is S or O;

whereby an unsaturated nitrogen containing compound is produced.

20. The process of claim 19 wherein the unsaturated nitrogen containing compound is selected from the group consisting of enamides, enamines, aryl amines and aryl amides.

21. The process of claim 19 wherein the compound containing —NH— or —$NH_2$— functional groups is selected from the group consisting of primary and secondary amides, anilines, imidazoles, carbamates, amidines, guanidines, amino thiazolines and ureas.

22. The process of claim 19 wherein the base is selected from the group consisting of 1,8-diazabicyclo[5.4.0]undec-7-ene and 1,5-diazabicyclo[4.3.0]non-5-ene.

23. The process of claim 19 wherein the catalyst precursor composition is a complex of $Ni(1,5\text{-cyclooctadiene})_2$ and a carbene of the formula

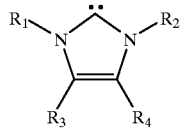

where $R^1$ and $R^2$ are independently selected from the group consisting of mesityl and adamantyl; and $R^3$ and $R^4$ are selected from the group consisting of methyl and hydrogen.

24. The process of claim 19 wherein X is chloride and $R_3$ is a phenyl group.

25. A process for the production of unsaturated nitrogen containing compounds comprising:

reacting the salt of a compound containing an —NH— or —NH$_2$— functional group next to a carbon sp$^2$ center with a compound of the formula

where X is either chloride, bromide, or iodide;

$R_1$ is either hydrogen, an alkyl group or an aryl group;

$R_2$ is independently selected from hydrogen, methyl or trimethylsilyl; and $R_3$ is an optionally substituted aryl group;

in the presence of a stoichiometric amount of a base and a catalyst composition comprising comprising a zero-valent nickel and a carbene ligand selected from the group consisting of

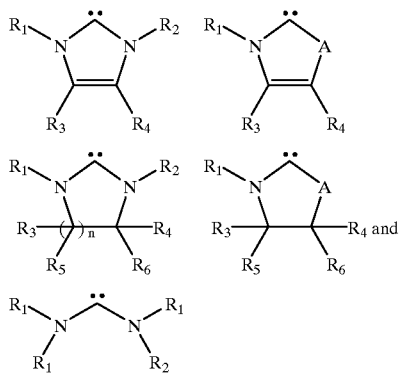

wherein:

$R^1$ and $R^2$ are each independently hydrocarbyl or substituted hydrocarbyl;

$R^3$, $R^4$, $R^5$ and $R^6$ are independently an element more electronegative than carbon, a substituted element more electronegative than carbon, hydrogen, hydrocarbyl, substituted hydrocarbyl or an inert functional group;

n is an integer from 1 to 4; and

A is S or O;

whereby an unsaturated nitrogen containing compound is produced.

26. The process of claim 25 wherein the unsaturated nitrogen containing compound is selected from the group consisting of enamides, enamines, aryl amines and aryl amides.

27. The process of claim 25 wherein the compound containing —NH— or —NH$_2$— functional groups is selected from the group consisting of primary and secondary amides, anilines imidazoles, carbamates, amidines, guanidines, amino thiazolines and ureas.

28. The process of claim 25 wherein the base is selected from the group consisting of 1,8-diazabicyclo[5.4.0]undec-7-ene and 1,5-diazabicyclo[4.3.0]non-5-ene.

29. The process of claim 25 wherein the catalyst precursor composition is a complex of Ni(1,5-cyclooctadiene)$_2$ and a carbene of the formula

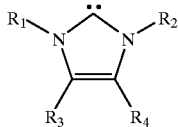

where $R^1$ and $R^2$ are independently selected from the group consisting of mesityl and adamantyl; and $R^3$ and $R^4$ are selected from the group consisting of methyl and hydrogen.

30. The process of claim 25 wherein X is chloride and $R_3$ is a phenyl group.

31. The process of claim 1 wherein the catalyst complex is formed in situ.

* * * * *